United States Patent
Kim

(10) Patent No.: US 11,045,301 B2
(45) Date of Patent: Jun. 29, 2021

(54) IMPLANTABLE MEDICAL DEVICE WITH COMPOUND STITCHING CONNECTION OF FRAMEWORK TO FABRIC

(71) Applicant: Cook Medical Technologies LLC, Bloomington, IN (US)

(72) Inventor: Woong Kim, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 80 days.

(21) Appl. No.: 16/299,359

(22) Filed: Mar. 12, 2019

(65) Prior Publication Data
US 2020/0289252 A1  Sep. 17, 2020

(51) Int. Cl.
*A61F 2/07* (2013.01)
*A61F 2/90* (2013.01)
*A61F 2/89* (2013.01)
*A61F 2/06* (2013.01)

(52) U.S. Cl.
CPC .......... *A61F 2/07* (2013.01); *A61F 2/90* (2013.01); *A61F 2/89* (2013.01); *A61F 2002/065* (2013.01); *A61F 2002/075* (2013.01); *A61F 2220/0016* (2013.01); *A61F 2220/0075* (2013.01); *A61F 2250/0037* (2013.01); *A61F 2250/0039* (2013.01)

(58) Field of Classification Search
CPC .......... A61F 2002/075; A61F 2220/075
See application file for complete search history.

(56) References Cited

U.S. PATENT DOCUMENTS

| | | | |
|---|---|---|---|
| 6,004,347 A * | 12/1999 | McNamara | A61F 2/07 606/194 |
| 7,175,652 B2 | 2/2007 | Cook et al. | |
| 7,238,198 B2 | 7/2007 | Hartley et al. | |
| 8,172,892 B2 | 5/2012 | Chuter et al. | |
| 8,348,988 B2 | 1/2013 | Lad et al. | |
| 8,897,892 B2 | 11/2014 | Fuhs et al. | |
| 9,700,400 B2 | 7/2017 | Havel | |
| 2004/0243221 A1* | 12/2004 | Fawzi | A61F 2/954 623/1.23 |
| 2005/0159804 A1 | 7/2005 | Lad et al. | |
| 2007/0055347 A1* | 3/2007 | Arbefeuille | A61F 2/07 623/1.15 |
| 2007/0207186 A1 | 9/2007 | Scanlon et al. | |
| 2009/0234430 A1* | 9/2009 | Fleming | A61F 2/07 623/1.13 |
| 2009/0318960 A1 | 12/2009 | Burkhart | |
| 2011/0071614 A1 | 3/2011 | Majercak et al. | |
| 2012/0197391 A1 | 8/2012 | Alkhatib et al. | |
| 2016/0235517 A1* | 8/2016 | Sethna | A61F 2/07 |
| 2020/0093590 A1* | 3/2020 | Reimer | A61F 2/2418 |

FOREIGN PATENT DOCUMENTS

EP    1752572    2/2007

* cited by examiner

*Primary Examiner* — Rebecca S Preston
(74) *Attorney, Agent, or Firm* — Liell & McNeil

(57) ABSTRACT

An implantable medical device, such as an aortic aneurism repair stent graft, includes a framework of struts that includes a plurality of vertices. A fabric is in contact with the framework, and attached to the fabric at each of the vertices with a respective compound stitching connection. The compound stitching connection includes a plurality of short span fixation stitches and a fan spread of long span tear resistance stitches.

17 Claims, 2 Drawing Sheets

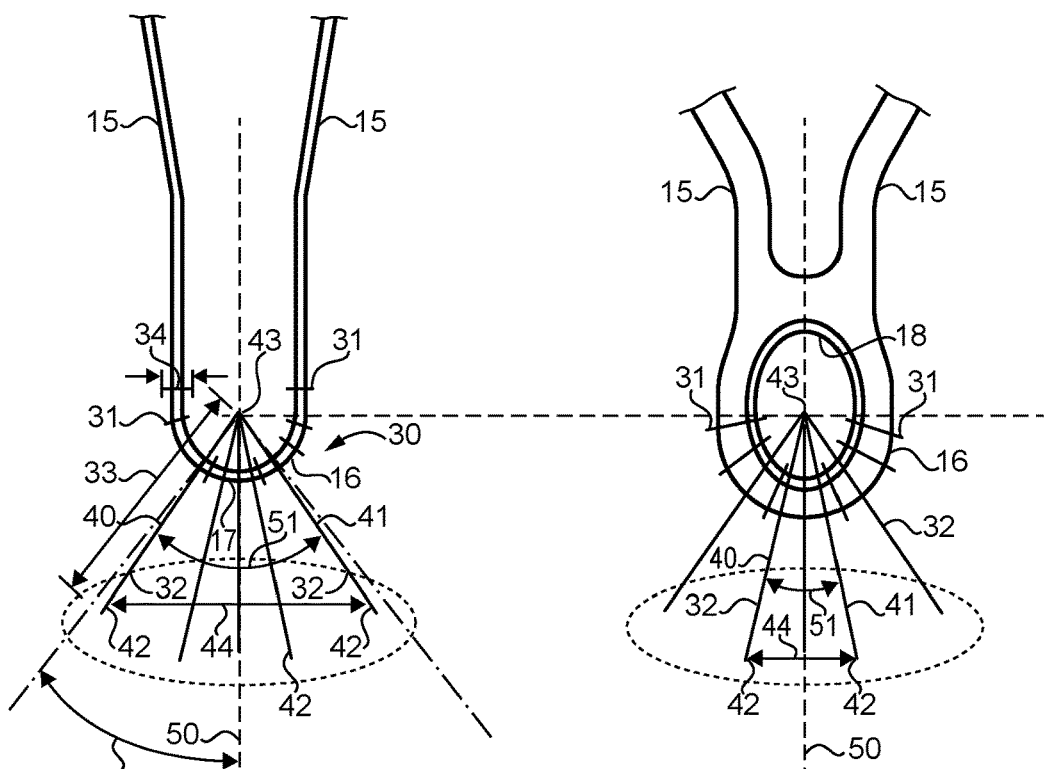
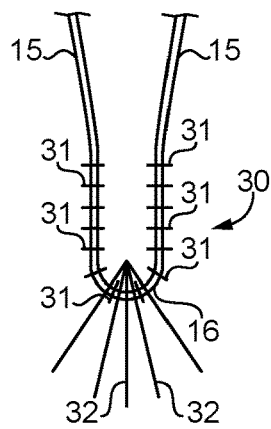
FIG. 5
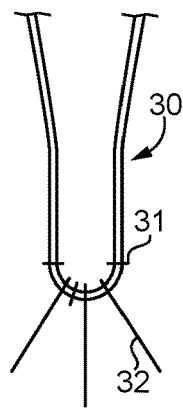
FIG. 6
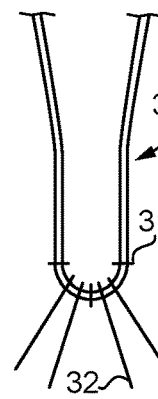
FIG. 7
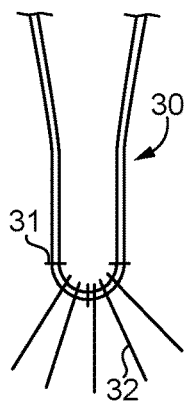
FIG. 8
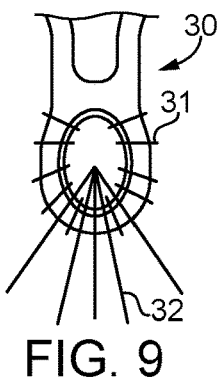
FIG. 9
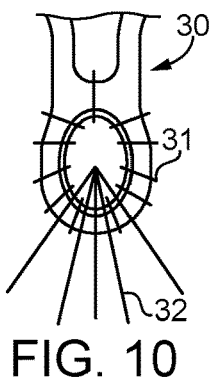
FIG. 10
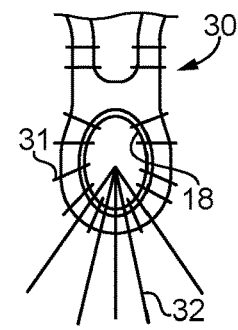
FIG. 11

IMPLANTABLE MEDICAL DEVICE WITH COMPOUND STITCHING CONNECTION OF FRAMEWORK TO FABRIC

TECHNICAL FIELD

The present disclosure relates generally to implantable medical devices that include fabric attached to a framework of struts, and more particularly to a compound stitching connection for attaching the framework of struts to a fabric, such as in a stent graft.

BACKGROUND

One class of implantable medical devices, including stent grafts and some heart valve replacements, include a fabric attached to a framework of struts with numerous fixation stitches. The sutured stitch connection serves to not only connect the framework to the fabric, but also to inhibit relative movement between the two. Although this class of implantable medical devices have performed well for many years, failures can sometimes occur. For instance, in some cases repeated flexing and/or blood flow forces can induce fatigue failure, with the fabric tearing responsive to stresses at the stitch entry points into the fabric. Although detachment of the fabric from the underlying stent framework is rare, fabric detachment can result in a catastrophic outcome.

The present disclosure is directed toward one or more of the problems set forth above.

SUMMARY

An implantable medical device, such as a stent graft, includes a framework of struts that includes a plurality of vertices. A fabric is in contact with the framework, and the framework is attached to the fabric at each of the vertices with a respective compound stitching connection. The compound stitching connection includes a plurality of fixation stitches and a plurality of tear resistance stitches.

BRIEF DESCRIPTION OF THE DRAWINGS

FIG. 3 is an enlarged schematic view of one compound stitching connection for the stent graft of FIGS. 1-2;

FIG. 4 is a schematic view of a compound stitching connection for a different framework vertex;

FIG. 5 is a schematic view of still another compound stitching connection;

FIG. 6 is a schematic view of a compound stitching connection;

FIG. 7 is a schematic view of still another compound stitching connection;

FIG. 8 is a schematic view of another compound stitching connection;

FIG. 9 is a schematic view of a compound stitching connection;

FIG. 10 is a schematic view of another compound stitching connection; and

FIG. 11 is a schematic view of still another compound stitching connection.

DETAILED DESCRIPTION

Figure 1:
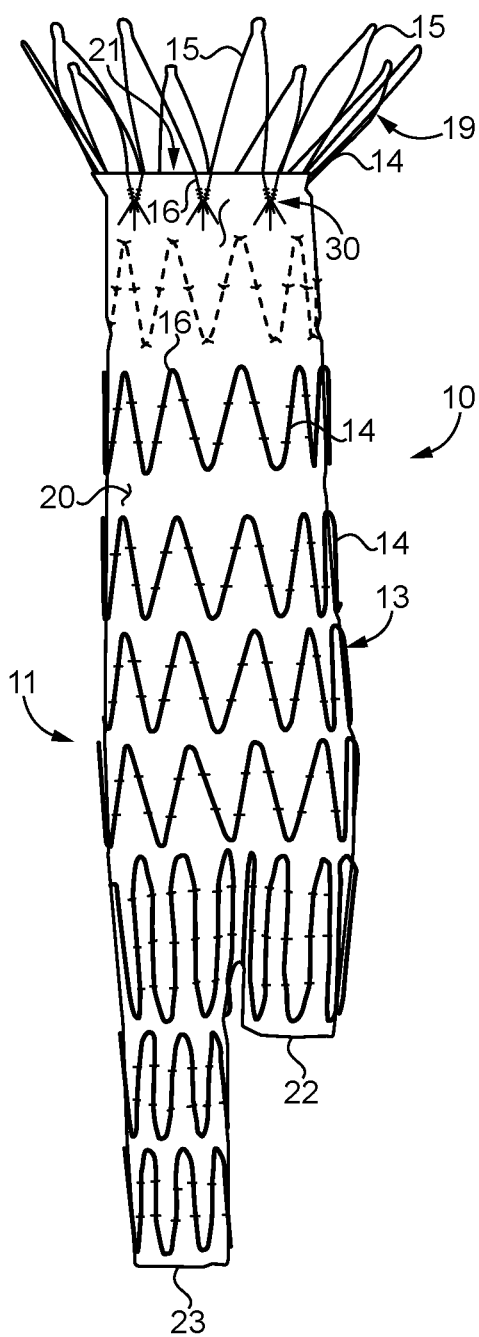
FIG. 1 is a front view of a stent graft according to the present disclosure.

Referring initially to FIG. 1, an implantable medical device 10 according to the present disclosure can be a stent graft 11, such as a stent graft for aortic aneurism repair. For instance, stent graft 11 may include a single inlet opening 21, that is positioned in a patient's aorta, and two outlet openings 22 and 23 that are received in the respective left and right iliac arteries, with the main body of the stent grafts spanning an aneurism in a manner well known in the art. It is important to note that stent graft 11 may include an anchoring portion 19, which may include barbs for holding stent graft 11 in place in the face of cyclic pressure and flow forces tending to push the stent graft 11 downstream. Thus, one could expect cyclic forces that can lead to fatigue problems especially where the anchoring portion 19 is attached to the fabric material 20 of stent graft 11. Although the present disclosure is being described in the context of a stent graft 11 for aortic aneurism repair, an implantable medical device according to the present disclosure could be a non-AAA stent graft or possibly even an artificial heart valve. In all instances, an implantable medical device 10 according to the present disclosure includes a framework 14 of struts 15 that includes a plurality of vertices 16, and a fabric 20 in contact with the framework. The present disclosure is about a compound stitching connection for attaching a framework 14 to fabric 20. However, not all the different portions of the framework may be subject to the same cyclic fatigue forces that could lead to fabric tearing as those associated with the stitching connection where the anchoring portion 19 is attached to fabric 20. Thus, the stent framework portions 14 in the main body of the stent graft 11 may have their stitching attachment unchanged for an implantable medical device according to the present disclosure, while the attachment of the anchoring portion 19 or some other portion may reflect a compound stitching connection according to the present disclosure.

Figure 2:
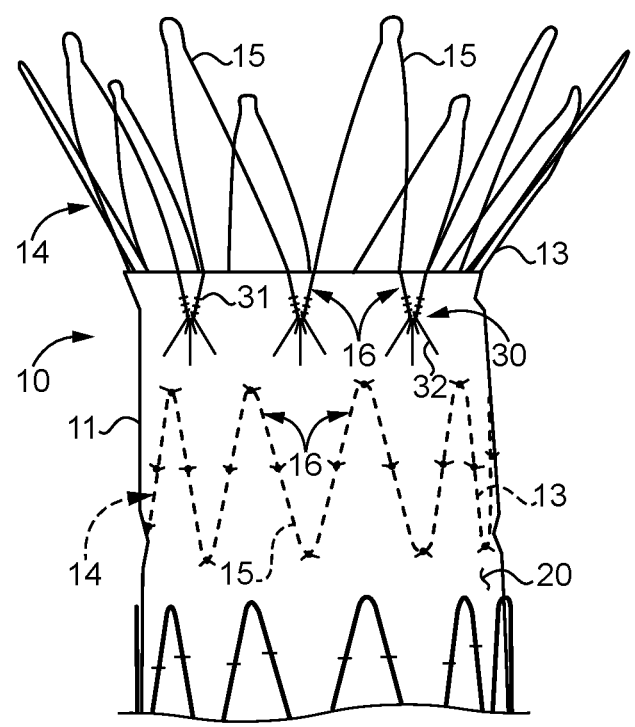
FIG. 2 is an enlarged partial schematic view of the stent graft from FIG. 1.

Referring in addition to FIGS. 2 and 3, stent graft 11 may be substantially identical to previously available stent grafts for aortic aneurism repair, except by the inclusion of compound stitching connections 30 between the fabric 20 and the vertices 16 of struts 15 that make up anchoring portion 19 of stent 13. A compound stitching connection 30 according to the present disclosure includes a plurality of fixation stitches 31 and a plurality of tear resistance stitches 32. Fixation stitches 31 are substantially identical to stitches used currently for attaching stents 13 to fabric 20; however, fixation stitches 31 in combination with tear resistance stitches 32 are new to this art. According to the present disclosure, a fixation stitch 31 may be differentiated from a tear resistance stitch 32 by their respective span distances. In particular, the span distance 34 of a fixation stitch 31 will always be less than a span distance 33 of a tear resistance stitch 32. The span distance 34 of each fixation stitch will often be about the same as a diameter of a strut 15 that contacts the given fixation stitch 31. Those skilled in the art will appreciate that a typical fixation stitch will pass through the fabric will form a U-shape, with the round portion contacting the strut on one side at a tangent, wrapping around the strut opposite to the side in contact with the fabric, and then leaving contact with the strut at a tangent on the opposite leg of the U-shape before re-penetrating the fabric 20. In particular, an average fabric span distance 33 of the tear resistance stitches 32 for a given stent graft 11 will be at least double an average fabric span distance 34 of the fixation stiches 31. Those skilled in the art will appreciate that the span distance 34 of fixation stiches is often not much more than the diameter of the strut 15 that the respective fixation stitch 31 contacts. Span distance means the distance between successive penetration points of a suture through the fabric in one stitch. Tear resistance stitches 32, on the other hand, will have an average span distance 34 that is at least double the average span distance 34 of the fixation stitches 31, but typically less than four times the average fabric span distance 34 of the fixation stitches 31.

The tear resistance stitches 32 may include a first tear resistance stitch 40 and a second tear resistance stitch 41 that each have a remote fabric penetration point 42 that is remote from a vertex fabric penetration point 43. The remote fabric penetration points 42 of the first and second tear resistance stitches 40 and 41 may be on respective sides of a line 50 that bisects the respective vertex 16. The remote fabric entry point 42 of the first tear resistance stitch 40 is separate from the remote fabric entry point 42 of the second tear resistance stitch 41 by a spread distance 44 that is greater than a span distance 34 of each of the fixation stitches 31. Those skilled in the art will appreciate that the vertex penetration point 43 of the tear resistance stitches 32 are relatively close to one another and may be closer to each other than the span distance 34 of the fixation stitches 31. The remote fabric penetration point 42 of the tear resistance stitches 32 are preferably spread apart so as to engage different crossing threads (weft and warp) that make up fabric 20. In addition, virtually any two tear resistance stitches 32 will define an acute spread angle 51. An acute angle according to the present disclosure is greater than zero. In most instances, the compound stitching connection 30 according to the present disclosure includes at least three fixation stitches 31 and at least three tear resistance stitches 32. In the embodiment of FIGS. 1-3, the compound stitching connection 30 includes five tear resistance stitches 32 and six fixation stitches 31. While in most cases the number of fixation stitches 31 in each compound stitching connection 30 will outnumber the number of tear resistance stitches 32, the present disclosure also contemplates compound stitching connections 30 that include more tear resistance stitches 32 than fixation stitches 31. As best shown in FIG. 3, each of the vertices 16 includes a hemispherical arc segment 17 of metallic material. As stated earlier, the vertices are defined by struts 15 that are portions of a framework 14, which in the illustrated embodiment is a stent 13 that is attached to a fabric 20 having a tubular shape sized to match stent 13.

Although the embodiment of FIGS. 1-3 show a framework 14 of struts 15 made up of deformed wire to produce a self expanding stent graft 11 of the type well known in the art, the present disclosure can also find potential application in stents having something other than a wire framework. For instance, FIG. 4 shows an example portion of struts 15 meeting at a vertex 16 that includes an enclosed eye 18 through which all of the tear resistance stitches 32 pass and maybe most or all of the fixation stitches 31 as well. The stent partially shown in FIG. 4 may be a laser cannula cut stent. Nevertheless, those with ordinary skill in the art will appreciate that other stent framework structures would also fall within the scope of the present disclosure. Like the embodiment of FIG. 3, the embodiment of FIG. 4 includes five tear resistance stitches 32 and six fixation stitches 31.

Referring now in addition to FIGS. 5-11, a variety of other compound stitching connections 30 according to the present disclosure are illustrated. FIG. 5 differs from the earlier embodiment by the inclusion of additional fixation stitches around the struts away from vertex 16. FIG. 6 is of interest for showing the compound stitching connection 30 that includes three fixation stitches 31 and three tear resistance stitches 32. FIG. 7 is of interest for being nearly identical to FIG. 6 except including four tear resistance stitches 32 and a lessor number, namely three, of fixation stitches 31. FIG. 8 shows a similar compound stitching connection 30 with three fixation stitches 31 and five tear resistance stitches 32. FIGS. 9, 10 and 11 show compound stitching connections 30 that are variants on the compound stitching connection shown in FIG. 4 with a cannula cut stent. FIG. 9 shows ten fixation stitches 31 and five tear resistance stitches 32. FIG. 10 shows eleven fixation stitches 31 and a nearly identical pattern of five tear resistance stitches 32 associated with FIG. 9. Finally, FIG. 11 shows a variant in which four fixation stitches 31 do not penetrate through the eye 18, but still constitutes a compound stitching connection 30 according to the present disclosure.

As best shown in FIG. 3, the spread angle of the outermost tear resistance stitch 32 compared to the vertex bisecting line 50 will form an angle that is 45° or less. The spread distance 44 between any two vertex fabric penetration points 43 of the tear resistance stitches 32 can be from zero to the distance between struts 15 that meet at vertex 16. The spread distance 44 between the remote fabric penetration points 42 of the tear resistance stitches 32 will almost always be greater than the span distance 34 of the fixation stitches 31. Compound stitching connections 30 according to the present disclosure will typically use the same medical grade suture material, such as a suitable monofilament for forming both the fixation stitches 31 and the tear resistance stitches 32. However, the different stitches that make up a compound stitching connection 30 could be of different materials without departing from the present disclosure. Thus, although not necessary, each compound stitching connection 30 may be made with exactly one continuous length of suture material.

Those skilled in the art will appreciate that by spreading out the remote fabric penetration points 42 of the tear resistance stitches 32, each individual stitch will engage with different combinations of weft and warp yarns that make up of the weave of fabric 20, thus enabling each individual stitch to greater contribute to the overall tear resistance of the compound stitching connection 30. Two key features that appear in all of the compound stitching connections 30 of the present disclosure includes a separation distance between remote fabric penetration points 42 of the tear resistance stitches combined with the span distance 33 of the tear resistance stitches greatly increasing the mean strength of the overall compound stitching connection 30 over prior art attachment strategies that relied only upon fixation stitches. Testing suggests that additional fixation stitches does not significantly increase the attachment strength between the fabric 20 and the framework 14, while the inclusion of tear resistance stitches 32 can increase an attachment connection strength two or three times greater than fixation stitches alone can achieve. Furthermore, not only are the connections made stronger using a compound stitching connection 30 according to the present disclosure, but sensitivity to failure of the connection is decreased. In other words, with fixation stitches alone, a failure can occur dramatically and completely resulting in a tear that separates the fabric from the underlying vertex 16 of the stent 13. Compound stitching connections 30 according to the present disclosure can result in an initial tearing causing the compound stitching connection 30 to actually increase in strength as the individual stitches all begin to contribute to the overall strength of the stitching connection as the tightest stitches initiate small tears, which increases tension in the less tight stitches. Thus, the compound stitching connection 30 of the present disclosure not only increases the overall strength of the connection between stent 13 and the fabric 20, but also provides a much more robust resistance to catastrophic failure that occurs when the fabric 20 actually tears free from an individual vertex connection 16. Compound stitching connections 30 according to the present disclosure permit the use of current low profile fabric and low profile monofilament sutures to achieve attachment strengths several times stronger than stitching connections that relied only upon fixation stitches while not significantly increasing the profile of the stent graft 11.

INDUSTRIAL APPLICABILITY

The present disclosure finds potential application in any implantable medical device in which a fabric is attached to an underlying framework of struts. The present disclosure finds particular application in fabric to strut connections that may undergo cyclic stresses that can lead to fatigue failure of stitches connecting the fabric to the underlying framework. The present disclosure finds potential application in the stitching connection between the anchoring portion of an aortic aneurism repair stent graft and the fabric of same. Nevertheless, the present disclosure could find potential application in other stent grafts or maybe even artificial heart valves that rely upon strut framework structures and attached fabric. Although the present disclosure is illustrated in the context of a fabric that is woven by the inclusion of weft and warp yarns that are oriented perpendicular to one another, other fabrics would also fall within the intended scope of the present disclosure.

The following definitions are not claims, but instead are intended to support multiple dependency type claims favored in Europe and elsewhere. 1. An implantable medical device comprising: a framework of struts that includes a plurality of vertices; a fabric in contact with the framework; the framework being attached to the fabric at each of the vertices with a respective compound stitching connection; the compound stitching connection includes a plurality of fixation stitches and a plurality tear resistance stitches. 2. The implantable medical device of definition 1 wherein an average fabric span distance of the tear resistance stitches is at least double an average fabric span distance of the fixation stitches. 3. The implantable medical device of any previous definition wherein the average fabric span distance of the tear resistance stitches is less than four times the average fabric span distance of the fixation stitches. 4. The implantable medical device of any previous definition wherein the plurality of tear resistance stitches includes first and second tear resistance stitches that each have a remote fabric penetration point that is remote from a vertex fabric penetration point; and the remote fabric penetration points are on respective sides of a line that bisects the respective vertex. 5. The implantable medical device of any previous definition wherein a first remote fabric entry point of the first tear resistance stitch is separated from a second remote fabric entry point of the second tear resistance stitch by a spread distance that is greater than a span distance of each of the fixation stitches. 6. The implantable medical device of any previous definition wherein the plurality of tear resistance stitches includes two tear resistance stitches that define an acute spread angle. 7. The implantable medical device of any previous definition wherein the compound stitching connection includes at least three fixation stitches and at least three tear resistance stitches. 8. The implantable medical device of any previous definition wherein the compound stitching connection includes more tear resistance stitches than fixation stitches. 9. The implantable medical device of any previous definition wherein the framework defines a stent; the fabric has a tubular shape sized to match the stent. 10. The implantable medical device of any previous definition wherein each of the vertices includes a hemispherical arc segment of metallic material. 11. The implantable medical device of any previous definition wherein each of the vertices includes an enclosed eye through which the fixation stitches and the tear resistance stitches pass. 12. An implantable stent graft comprising: a framework of struts that defines a tubular shape includes a plurality of vertices; a fabric with a tubular shape in contact with the framework; the framework being attached to the fabric at each of the vertices with a respective compound stitching connection; the compound stitching connection includes a plurality of fixation stitches and a plurality of tear resistance stitches. 13. The implantable stent graft of definition 12 wherein an average fabric span distance of the tear resistance stitches is at least double an average fabric span distance of the fixation stitches; and the average fabric span distance of the tear resistance stitches is less than four times the average fabric span distance of the fixation stitches. 14. The implantable stent graft of any of definitions 12-13 wherein the plurality of tear resistance stitches includes first and second tear resistance stitches that each have a remote fabric penetration point that is remote from a vertex fabric penetration point; the remote fabric penetration points are on respective sides of a line that bisects the respective vertex; and a first remote fabric entry point of the first tear resistance stitch is separated from a second remote fabric entry point of the second tear resistance stitch by a spread distance that is greater than a span distance of each of the fixation stitches. 15. The implantable stent graft of any of definitions 12-14 wherein the first and second resistance stitches that define an acute spread angle. 16. The implantable stent graft of any of definitions 12-15 wherein the compound stitching connection includes at least three fixation stitches and at least three tear resistance stitches. 17. The implantable stent graft of any of definitions 12-16 wherein the compound stitching connection includes more tear resistance stitches than fixation stitches.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:
1. An implantable medical device comprising:
a framework of struts that includes a plurality of vertices;
a fabric in contact with the framework;
the framework being attached to the fabric at each of the vertices with a respective compound stitching connection;
each respective compound stitching connection includes a plurality of fixation stitches and a plurality tear resistance stitches; and
wherein an average fabric span distance of the tear resistance stitches is at least double an average fabric span distance of the fixation stitches.
2. The implantable medical device of claim 1 wherein the average fabric span distance of the tear resistance stitches is less than four times the average fabric span distance of the fixation stitches.
3. An implantable medical device comprising:
a framework of struts that includes a plurality of vertices;
a fabric in contact with the framework;

the framework being attached to the fabric at each of the vertices with a respective compound stitching connection;

each respective compound stitching connection includes a plurality of fixation stitches and a plurality tear resistance stitches;

wherein each of the tear resistance stitches penetrates through the fabric at successive penetration points that are separated by a span distance, and each of the fixation stitches penetrates through the fabric at successive penetration points that are separated by a span distance that is less than the span distance of each of tear resistance stitches;

wherein each of the fixation stitches wraps around one of the struts to form a U-shape;

wherein the plurality of tear resistance stitches includes first and second tear resistance stitches that each have a remote fabric penetration point that is remote from a vertex fabric penetration point; and the remote fabric penetration points are on respective sides of a line that bisects the respective vertex.

4. The implantable medical device of claim 3 wherein a first remote fabric entry point of the first tear resistance stitch is separated from a second remote fabric entry point of the second tear resistance stitch by a spread distance that is greater than the span distance of each of the fixation stitches.

5. An implantable medical device comprising:
a framework struts that includes a plurality of vertices;
a fabric in contact with the framework;
the framework being attached to the fabric at each of the vertices with a respective compound stitching connection;
each respective compound stitching connection includes a plurality of fixation stitches and a plurality tear resistance stitches;
wherein each of the tear resistance stitches penetrates through the fabric at successive penetration points that are separated by a span distance, and each of the fixation stitches penetrates through the fabric at successive penetration points that are separated by a span distance that is less than the span distance of each of the tear stance stitches; and
wherein each of the fixation stitches wraps around one of the struts to form a U-shape; and
wherein each respective compound stitching connection includes at least three fixation stitches and at least three tear resistance stitches.

6. The implantable medical device of claim 5 wherein the each respective compound stitching connection includes more tear resistance stitches than fixation stitches.

7. An implantable medical device comprising:
a framework of struts that includes a plurality of vertices;
a fabric in contact with the framework;
the framework being attached to the fabric at each of the vertices with a respective compound stitching connection;
each respective compound stitching connection includes a plurality of fixation stitches and a plurality tear resistance stitches;
wherein each of the tear resistance stitches penetrates through the fabric at successive penetration points that are separated by a span distance, and each of the fixation stitches penetrates through the fabric at successive penetration points that are separated by a span distance that is less than the span distance of each of tear resistance stitches;
wherein the fixation stitches form a U-shape;

wherein each of the vertices includes an enclosed eye through which the fixation stitches and the tear resistance stitches pass.

8. An implantable stent graft comprising:
a framework of struts that defines a tubular shape and includes a plurality of vertices;
a fabric with a tubular shape in contact with the framework;
anchoring portions of the framework being attached to the fabric at each of the vertices with a respective compound stitching connection;
each respective compound stitching connection includes a plurality of fixation stitches and a plurality of tear resistance stitches; and
wherein each of the tear resistance stitches penetrates through the fabric at successive penetration points that are separated by a span distance, and each of the fixation stitches penetrates through the fabric at successive penetration points that are separated by a span distance that is less than the span distance of each of the tear resistance stitches;
wherein an average of the span distances of the tear resistance stitches is at least double an average of the span distances of the fixation stitches; and
the average of the span distances of the tear resistance stitches is less than four times the average of the span distances of the fixation stitches.

9. The implantable stent graft of claim 8 wherein the plurality of tear resistance stitches includes first and second tear resistance stitches that each have a remote fabric penetration point that is remote from a vertex fabric penetration point;
the remote fabric penetration points are on respective sides of a line that bisects the respective vertex; and
a first remote fabric entry point of the first tear resistance stitch is separated from a second remote fabric entry point of the second tear resistance stitch by a spread distance that is greater than the span distance of each of the fixation stitches.

10. The implantable stent graft of claim 9 wherein the first and second tear resistance stitches define an acute spread angle.

11. The implantable stent graft of claim 8 wherein the each respective compound stitching connection includes at least three fixation stitches and at least three tear resistance stitches.

12. The implantable stent graft of claim 7 wherein the each respective compound stitching connection includes more tear resistance stitches than fixation stitches.

13. An implantable stent graft comprising:
a framework of struts that defines a tubular shape and includes a plurality of vertices;
a fabric with a tubular shape in contact with the framework;
anchoring portions of the framework being attached to the fabric at each of the vertices with a respective compound stitching connection;
each respective compound stitching connection includes a plurality of fixation stitches and a plurality of tear resistance stitches; and
wherein each of the tear resistance stitches penetrates through the fabric at successive penetration points that are separated by a span distance, and each of the fixation stitches penetrates through the fabric at successive penetration points that are separated by a span distance that is less than the span distance of each of the tear resistance stitches;

wherein the tubular shape of the fabric includes a single inlet opening and two outlet openings.

14. The implantable medical device of claim 13 wherein the plurality of tear resistance stitches includes two tear resistance stitches that define an acute spread angle.

15. The implantable medical device of claim 13 wherein the framework defines a stent;

the fabric has a shape sized to match the stent.

16. The implantable medical device of claim 13 wherein each of the vertices includes a hemispherical arc segment of metallic material.

17. The implantable medical device of claim 13 where the anchoring portions includes barbs.

* * * * *